United States Patent
Park et al.

[11] Patent Number: 5,980,720
[45] Date of Patent: Nov. 9, 1999

[54] METHODS OF TREATING CRYSTAL-GROWN WAFERS FOR SURFACE DEFECT ANALYSIS

[75] Inventors: Jung-min Park, Seoul; Jae-gun Park, Kyungki-do; Gon-sub Lee, Kyungki-do; Gi-jung Kim, Kyungki-do, all of Rep. of Korea

[73] Assignee: Samsung Electronics Co., Ltd., Rep. of Korea

[21] Appl. No.: 08/977,639

[22] Filed: Nov. 24, 1997

[30] Foreign Application Priority Data

Feb. 6, 1997 [KR] Rep. of Korea .......................... 97-3764

[51] Int. Cl.⁶ ................ C25D 5/02; C25D 5/00; C25D 7/12; B32B 35/00
[52] U.S. Cl. ............ 205/118; 205/81; 205/120; 205/123; 205/135; 205/157; 205/149; 205/210; 427/140; 427/309; 427/282; 438/928; 438/687
[58] Field of Search ............... 205/81, 120, 123, 205/135, 157, 149, 118, 210; 427/140, 309, 282; 438/928, 687

[56] References Cited

U.S. PATENT DOCUMENTS 5,783,495 7/1998 Li et al. ................................. 438/738

OTHER PUBLICATIONS

Itsumi et al., "Copper Decoration Method to Locate the Defects in Gate Oxide Film", Oyo Butsuri, vol. 65, No. 11, pp. 1164–1165. (Abstract), no month available 1996.

Tuyen, "Study of Surface Treatment Using the Surface Photovoltaic Method", Phys. Halbleiteroberflaeche, vol. 13, pp. 151–155. (Abstract only), no month available 1982.

Primary Examiner—Kathryn Gorgos
Assistant Examiner—Edna Wong
Attorney, Agent, or Firm—Myers, Bigel, Sibley & Sajovec

[57] ABSTRACT

Methods of treating wafers for analyzing defects present therein comprise providing wafers having front side surfaces comprising defective portions and a back side surfaces opposite thereto; and decorating the defective portion of the front side of the wafer with copper.

24 Claims, 5 Drawing Sheets

METHODS OF TREATING CRYSTAL-GROWN WAFERS FOR SURFACE DEFECT ANALYSIS

FIELD OF THE INVENTION

The invention relates to methods of analyzing wafer defects, and more particularly to methods of treating wafers for defect analysis.

BACKGROUND OF THE INVENTION

With the increasing complexity of integrated circuit (e.g., semiconductor) devices, the quality of the wafers upon which the integrated circuits are positioned may be significant. Wafer quality is typically important in achieving desirable device yield and reliability.

Conventional wafer quality usually depends on a number of factors. For example, the quality is often influenced by the quantity of defects present in the wafer. Defects are typically generated during crystal growth. The wafer defects may generally be divided into two types: (1) defects arising from particle contamination and (2) crystal defects originating from silicon ingot growth.

During typical semiconductor wafering processes, single crystal silicon is usually formed by employing a multi-step process on a raw material such as quartzite, for example. The raw material may then be grown into a single crystal ingot by a suitable technique such as a Czochralski (CZ) method or a Float Zone (FZ) method.

An array of patterning and polishing processes are then typically carried out on the grown single crystal ingot. A wafer designed for use in an integrated circuit device is subsequently formed. In particular, the surface of the single crystal ingot is typically trimmed down in attempting to achieve proper size and morphology. After the ingot surface is examined, typically by an x-ray technique, the trimmed ingot may then be adjusted for orientation flattening along the lengthwise direction of the ingot. Typically, ingot etching is subsequently performed in order to potentially remove contaminants which may exist on the ingot surface. The ingot may then be sawed to form silicon slices or wafers. An edge-rounding technique can next be carried out on the edge of the silicon wafers, and a lapping technique may thereafter be performed on the wafer to minimize wafer bending. Contamination which may be present on the slice can be removed by employing a suitable chemical etching technique such as, slice etching, for example.

Next, the wafer is usually subjected to a thermal processing technique known as "donor killing". The "donor killing" process is designed to prevent interstitial oxygen from serving as a donor subsequent to ingot growth. The process is intended to minimize any complications with respect to wafer electrical control that may result in an integrated circuit device.

After the donor killing process, the surface of the wafer is typically polished and cleaned by chemical or mechanical means. Defects or orientations which may be present in the wafer can then be examined. The wafer is then typically subjected to an inspection and, if acceptable, the wafer is packaged for commercial use.

A conventional cleaning process, however, may be limited in the types of contaminants and impurities that it can remove. More particularly, although contaminants such as dust may be removed, potential faults in the wafer like D-defects, oxygen precipitates, stacking faults, and metallic precipitates may not be addressed by the above cleaning process.

Potentially troublesome defects include, for example, COPs ("Crystal Oriented Particles") known as micropits, along with D-defects. As known in the art, "D-defects are defined as deformation defects, namely defects that propagate three-dimensionally so as to disrupt the crystal lattice structure. These defects often adversely affect the yield and reliability of integrated circuit devices, since the defects can impact manufacturing processes involved in producing the devices. Thus, it is typically important to examine the density and deflection distribution of the wafer surface, along with the morphology of the surface. Based on these analyses, adjustments may be made which can allow for increases in device yield prior to a device being used in a wafer.

A conventional method for examining potential wafer surface defects involves laser scattering particle counter (LSPC) technology. In the above method, a bare wafer is typically cleaned with, for example, a solution of SC1 (i.e., ammonium hydroxide, hydrogen peroxide, and water having a molar ratio of 1:1:8 respectively), along with hydrogen fluoride. Subsequently, a constant wavelength laser is typically irradiated on the bare wafer by a laser scattering particle counter. Scattered signal data is then typically generated. As a result, the surface defects of the wafer may be examined.

There are potential problems associated with the above method. First, it is often difficult to accurately measure the amount and distribution of COPs on a wafer. More particularly, COPs are typically found only on the vacancy-rich area of the wafer. As a result, it is often necessary to measure the real diameter of the vacancy-rich area from a COP map acquired by a laser scattering particle counter. When a bare wafer is cleaned with a SC1/hydrogen fluoride solution, however, it may be difficult to distinguish real contamination from the COPs. Moreover, particles often accumulate on defects during COP mapping, and the presence of the particles may distort the level of defects measured from the wafer. Second, it may be difficult to fully detect the defects due to limitations in the conventional scattering particle counters. A conventional scattering particle counter usually has a detection limit of 0.12 $\mu$m, and as a result COPs of smaller size may not be observed. Since smaller defects are often found in the peripheral regions of vacancy-rich areas in the wafer, it may be extremely difficult to accurately measure the diameter of the vacancy-rich area. Third, a conventional scattering particle counter technique is often unable to accurately access the size and morphology of wafer defects and, as a result, their position on the wafer surface. Conventionally, defect position is usually observed via the coordination between a LSPC technique and an AFM (atomic force microscope) technique. Nonetheless, the size and defects determined by using an AFM technique may be larger than the size and defects measured by the LSPC technique. Thus, the size, morphology, and location of the defects may not be accurately determined.

There remains a need in the art to address the potential difficulties associated with conventional methods of analyzing wafer defects.

SUMMARY OF THE INVENTION

It is an object of the present invention to provide methods of treating wafers for analyzing the size and morphology of defects present therein more accurately than determined by conventional techniques.

It is another object of the present invention to provide methods of treating wafers for analyzing defects present therein which allows for an increase in the detection capacity of the wafers relative to conventional detection techniques.

It is yet another object of the present invention to provide methods of treating wafers for analyzing defects therein by visual inspection.

These and other objects and advantages are provided by the present invention. In a first aspect, the invention provides methods of treating wafers for analyzing defects which comprise providing wafers having front side surfaces and back side surfaces opposite thereto. The front side surfaces comprise defect-containing portions. The defect-containing portions on the front sides of the wafers are then decorated with copper to allow the wafers to be analyzed.

In a second aspect, the invention provides other methods of treating wafers. The methods comprise providing wafers having front side surfaces comprising defect-containing portions and back side surfaces opposite thereto. Insulation films are then formed on the front side surfaces of the wafers. The back sides of the wafers and the insulation films are removed from the wafers to expose the defect-containing portions. The exposed defect-containing portions of the wafers are decorated with electrolytes such that the wafers may be subsequently analyzed.

DETAILED DESCRIPTION OF THE PREFERRED EMBODIMENTS

Figure 1:
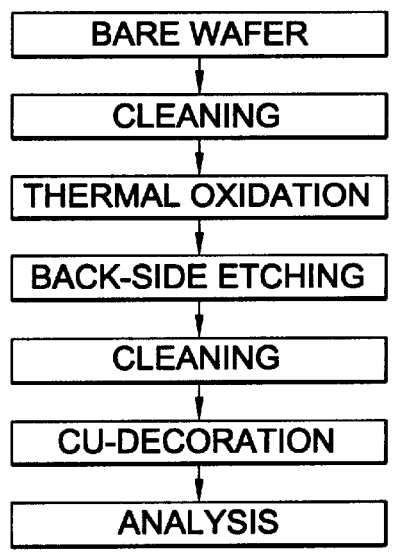
FIG. 1 is a processing chart illustrating a method of analyzing wafer defects according to an embodiment of the present invention.

The present invention now will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In a first aspect, the invention provides methods of treating wafers for analyzing defects present therein. The methods comprise providing wafers having front side surfaces and back side surfaces opposite thereto. The front side surfaces comprise defect containing portions. Insulation films are preferably formed on the front side surfaces of the wafers, and the back sides of the wafers (preferably portions of the back sides) are preferably etched. The etching steps are preferably performed using hydrogen fluoride in the gaseous phase. The defective portions on the front sides of the wafers are then decorated with copper to allow the wafers to be analyzed.

The wafers which are utilized in the methods of the invention are numerous. Preferably, the wafers are single crystal wafers comprising silicon obtained by processes known in the art such as, for example, the Czochralski (CZ) technique.

The methods may include steps in addition to those described above. For example, the methods can further comprise cleaning the front side surfaces of the wafers prior to the steps of forming the insulation films on the wafers. The cleaning steps can be performed by known and accepted techniques. For example, the cleaning steps can be performed by contacting the wafers with aqueous solutions comprising ammonium hydroxide, hydrogen peroxide, and hydrogen fluoride. The wafers, namely the back side of the wafers, may be cleaned after the etching steps are performed. As an illustration, the wafers may be cleaned with water, preferably deionized water.

In accordance with the invention, the decoration steps are preferably carried out by loading dummy wafers inside decoration devices. The decoration devices comprise upper plates, lower plates and side walls positioned between and surrounding the upper and lower plates. The upper and lower plates comprise copper. Electrolytes, preferably methanol, are then injected into the devices. The copper in the upper and lower plates are then oxidized by applying voltages to the plates. The voltages preferably range from about 3 MV/cm to about 10 MV/cm. The dummy wafers are then unloaded from the decoration devices, and the etched wafers are loaded into the decoration devices. Voltages are then applied to the upper and lower plates of the decoration devices, preferably ranging from about 3 MV/cm to about 10 MV/cm. The defective portions of the front sides of the wafers thus become decorated with copper.

The insulation films are preferably oxide films formed by a number of accepted and known techniques. The oxide films, for example, may be formed by chemical vapor deposition (CVD) methods, thermal treatment methods, and the like. The insulation films are preferably constant in thickness. The thicknesses of the insulation films preferably range from about 250 Å to about 1500 Å, more preferably from about 500 Å to about 1200 Å. Most preferably, the oxide films have thicknesses of 1000 Å.

The invention also relates to other methods of treating wafers for analyzing defects present thereon. The methods comprise providing wafers having front side surfaces comprising defect-containing portions and back side surfaces opposite thereto; forming insulation films on the front side surfaces of the wafers; etching the back side surfaces of the wafers; removing the insulation films from the wafers to expose the defect-containing portions; and decorating the exposed defect-containing portions of the wafers with electrolytes. Electric fields may be formed on the front and back sides of the wafers to further assist in preparing the wafers for analyses. The electric fields typically range from about 3 MV/cm to about 10 MV/cm. The above methods may also encompass the embodiments described hereinabove.

The defects present in the wafers treated according to the methods of the invention can be analyzed using various techniques. In particular, the density and distribution of the defects can be examined by visual inspection without the aid of magnification. The defect morphology may be analyzed by employing an electron microscope. A vast number of defects can be analyzed such as, but not limited to, D-defects, crystal oriented particle defects, and mixtures thereof.

The invention will now be described in greater detail with reference to the drawings. Referring to FIG. 1, a processing chart illustrating a method of analyzing wafer defects according to an embodiment of the invention is presented. The bare wafer depicted in this illustration was grown by the Czocharalski technique. The bare wafer was cleaned with an SC1 solution (i.e., ammonium hydroxide, hydrogen peroxide, and water) in combination with hydrogen fluoride to remove contamination (e.g., particles) that exist on the wafer. The bare wafer was then thermally oxidized in an electric furnace. The thickness of the resulting oxidized film ranged from about 250 Å to about 1500 Å. Given this thickness range, a Cu-decoration step may be readily performed with minimal potential complications. In the event the thickness of the thermally oxidized film is between about 500 Å to about 1200 Å, the power used in applying the electric field should be well controlled. It is most desirable for the oxidized film to have a thickness of about 1000 Å for optical defect analysis.

During the Cu-decoration step, a portion of the back side of the oxidized film is etched to establish an electrical connection between upper and lower portions of the back side. It should be noted that the entire back side may be etched if desired. In this instance, hydrogen fluoride vapor is used for etching. Subsequently, water (e.g., deionized water) is used to clean the wafer such that remaining residues (e.g., etching gas, etc.) are removed.

Figure 2:
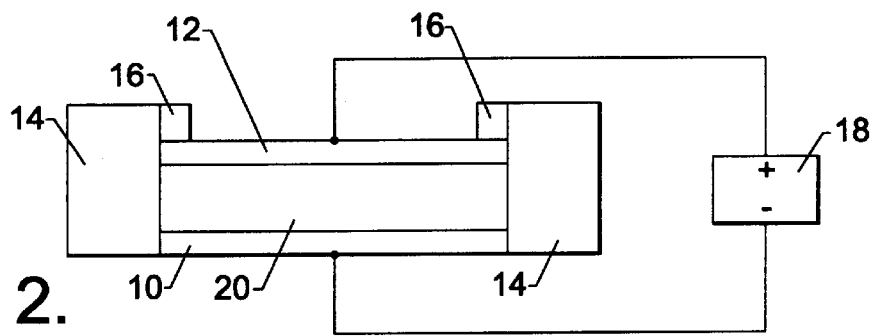
FIG. 2 is a schematic representation illustrating a copper (Cu) decoration device for performing the Cu decoration operation set forth in FIG. 1.

Thereafter, a decoration step is performed on the wafer which contains the oxide film. FIG. 2 provides a schematic of the device used in the decoration step. A further description of this device is provided in Korean Patent Application Number 95-52723 entitled "Method of Analyzing an Oxide Film formed on a Wafer by Cu-Decoration" filed Dec. 20, 1995. Referring to FIG. 2, the device has an upper plate 12 and a lower plate 10 each containing Cu and four surrounding side walls 14 which form a chamber, more specifically, a wafer mounting part 20. The upper plate 12 and the lower plate 10 have their own terminals which are connected via an external power source 18. An electrical field is formed between the upper and lower plates by applying variable power through each of the terminals. A capping part 16 is mounted along the edge of the upper plate 12 for affixing the upper plate to the side walls 14. In FIG. 2, the side walls 14 and the capping part 16 are made of an insulation material such as tetrafluoroethylene (TEFLON®).

The wafer mounting part 20 is designed to have enough space to allow for the loading and unloading of a wafer. Additionally, the wafer mounting part 20 may be sealed after an electrolyte is supplied to a wafer contained therein.

Figure 3:
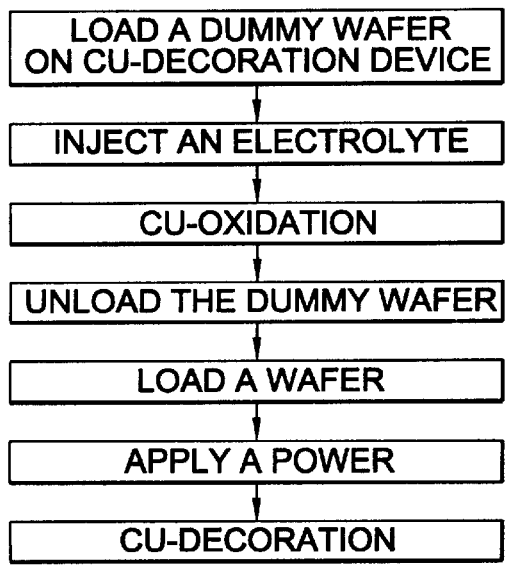
FIG. 3 is a processing chart illustrating the Cu-decoration operation set forth in FIG. 1.

The process set forth in FIG. 1 is now described in greater detail with reference to FIG. 3. A dummy wafer is first mounted on the lower plate 10 of the device illustrated in FIG. 2. The dummy wafer contains an oxide film thereon having a thickness of 1000 Å, and is installed in the device upon lifting off upper plate 12. Next, methanol is introduced into the wafer mounting part 20 of the device. The plates become dipped in the methanol, and are then oxidized with an applied negative bias as set forth below:

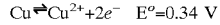
$Cu \rightleftharpoons Cu^{2+} + 2e^-$  $E^o = 0.34$ V

During the Cu decoration procedure, the electric field applied on the upper and lower plates preferably ranges from about 3 to about 10 MV/cm, although other values may be used. In this embodiment, an electric field of 5 MV/cm is applied for 1 hour.

The dummy wafer is unloaded, and a wafer which is to be processed is loaded in the wafer mounting part 20. An electric field is applied on the upper and lower plates, and the defect side of the wafer is decorated with Cu. The strength of the applied electric field ranged from about 3 to about 10 MV/cm, and was adjusted for the initial 10 minutes of application. Although Applicants do not wish to bound by any theory, it is believed that the mechanism for Cu-deterioration involves local oxide thinning along the edge of the wafer surface defects as a result of the thermal oxidation described in FIG. 1. As a negative bias is applied on the lower plate 10, a breakdown of the oxide film occurs. The reduced Cu-positive ions in the electrolyte solution are deposited on the defect-containing site on the wafer, and the deposited Cu diffuses into the silicon bulk of the wafer to decorate the wafer as the Cu precipitates.

Figure 4:
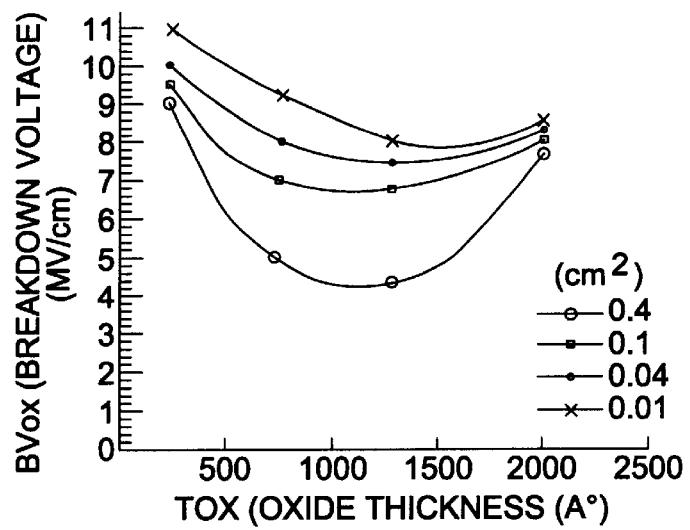
FIG. 4 is a graph illustrating the relationship between the thickness of a grown oxide film and the breakdown voltage thereafter according to the present invention.
Figure 5:
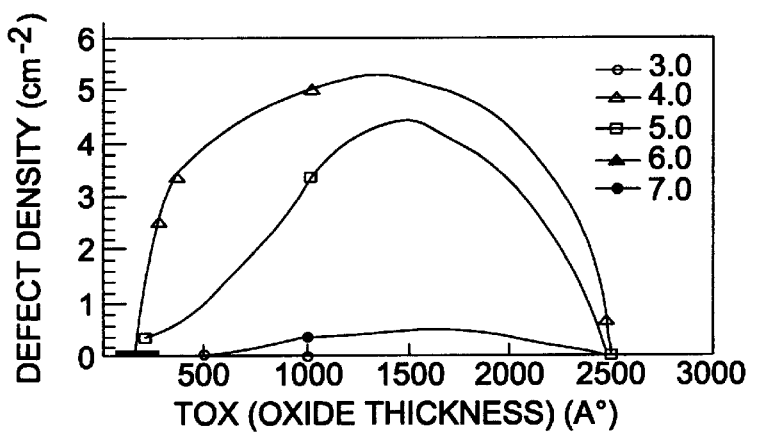
FIG. 5 is a graph illustrating the relationship between the thickness employed in detecting the density characteristics of a grown oxide film and the electric field applied thereto according to the present invention.
Figure 6:
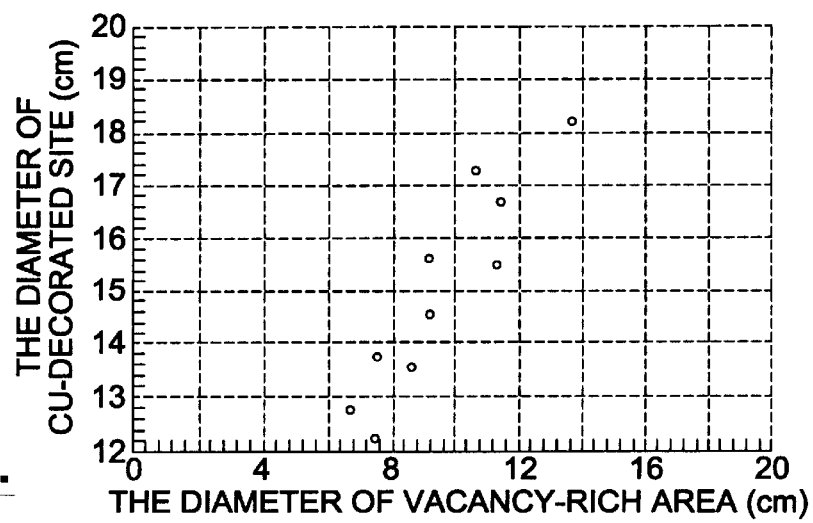
FIG. 6 is a graph illustrating the relationship between the diameter of a vacancy-rich area on a wafer determined by a conventional COP map and the diameter of a Cu-decorated area on a wafer determined according to the present invention.

After Cu-decoration, analysis of the wafer density, distribution of the wafer defects, and morphology of the wafer defects, are carried out. FIGS. 4 through 6 present the data relating to breakdown voltage, defect density, and Cu-decorated site diameter versus the thickness of an oxide film according to the invention. Specifically, FIG. 4 illustrates the relationship between the thickness of the grown oxide film and the breakdown voltage determined thereafter. The leakage current is defined as $-10$ $\mu$A/capacitor, and the capacitor width is varied as values of 0.4, 0.1, 0.04, and 0.01 cm$^2$ are employed.

Examining FIG. 4, the thickness of the oxide film and the breakdown voltage are correlated. As illustrated, the breakdown voltage decreases between 250 Å and 1000 Å, and thereafter increases.

FIG. 5 is a graph illustrating the relationship between the thickness used in detecting the density characteristics of a grown oxide film and the electric field applied thereto according to the present invention. As shown, the defect density of the oxide film increases as the voltage increases from 3.0 MV/cm to 7.0 MV/cm for the same oxide film. As the thickness of the oxide film increases for the same applied voltage, the defect density increases, and then decreases over the thickness of an inflection.

FIG. 6 is a graph illustrating the relationship between the diameter of a vacancy-rich area on a wafer determined by a conventional COP map and the diameter of a Cu-decorated area on a wafer. As shown, the diameter of the vacancy-rich area of a conventional laser scattering counter increases as the diameter of a Cu-decorated site increases. Thus, the invention is capable of providing good analytical results with respect to wafer defects.

Moreover, the detection limit of the present invention represents a potential improvement over the prior art. More particularly, the maximum detection limit of a conventional laser scattering counter was 0.12 $\mu$m even for intervals of COPs ranging in size from 0.12–0.16 $\mu$m; 0.16–0.20 $\mu$m; and 0.20–0.24 $\mu$m. In contrast, the methods of the invention may be able to analyze defects having particle sizes as low as 0.06 $\mu$m.

Figure 7:
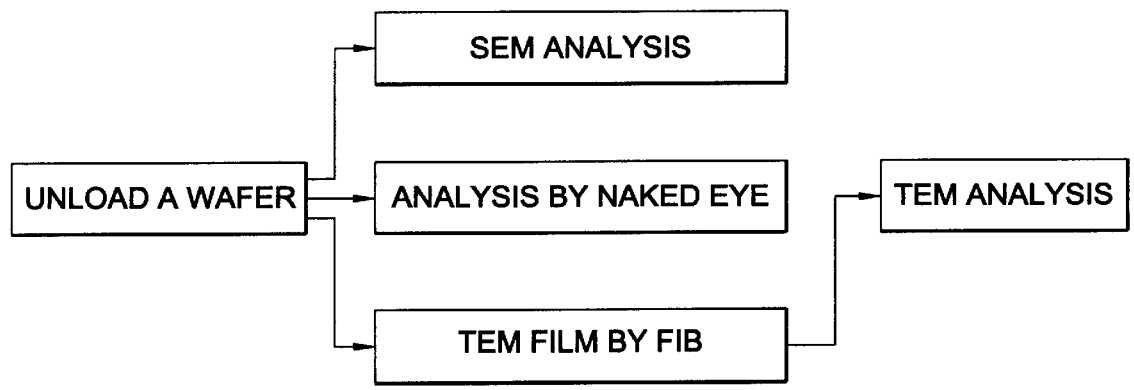
FIG. 7 is a diagram illustrating the steps set forth in FIG. 1.

Referring now to FIG. 7, the analysis steps illustrated in FIG. 1 are set forth. In accordance with the invention, the Cu-decorated site may be examined without the aid of magnification. Moreover, the density, distribution, and morphology of crystal defects can be examined by scanning electron microscopy (SEM) and transverse electric and magnetic (TEM) methods. Prior to a TEM analysis, it may be necessary to prepare a wafer sample by utilizing a focus ion beam (FIB).

Figure 8:
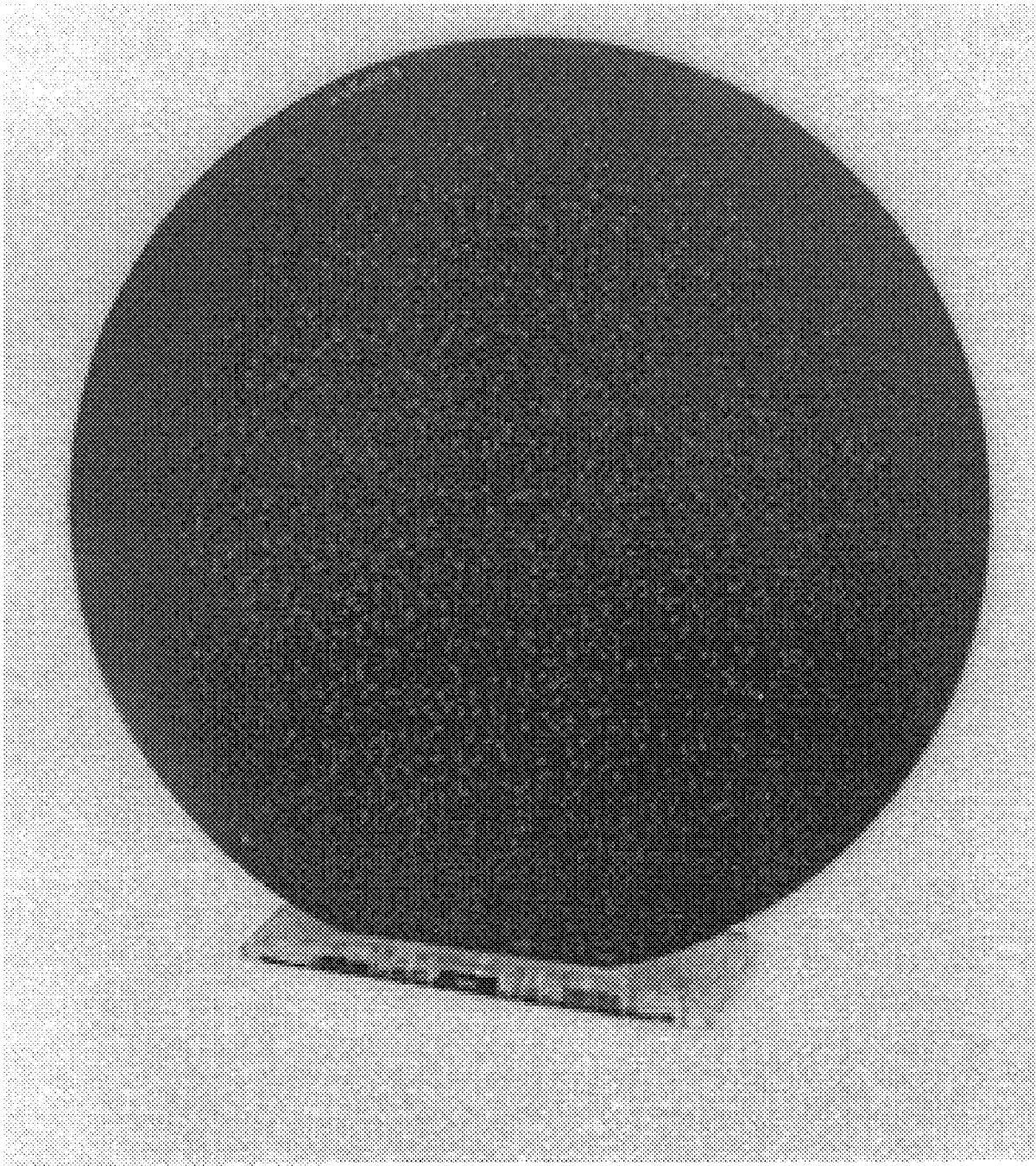
FIG. 8 is a photograph depicting the state of a Cu-decorated site on a wafer.

FIG. 8 is a photograph illustrating the state of a Cu-decorated site on a wafer. The distribution of the Cu-decorated site may be examined without magnification, and therefore the density of the defects may be evaluated in a like manner.

Figure 9A:
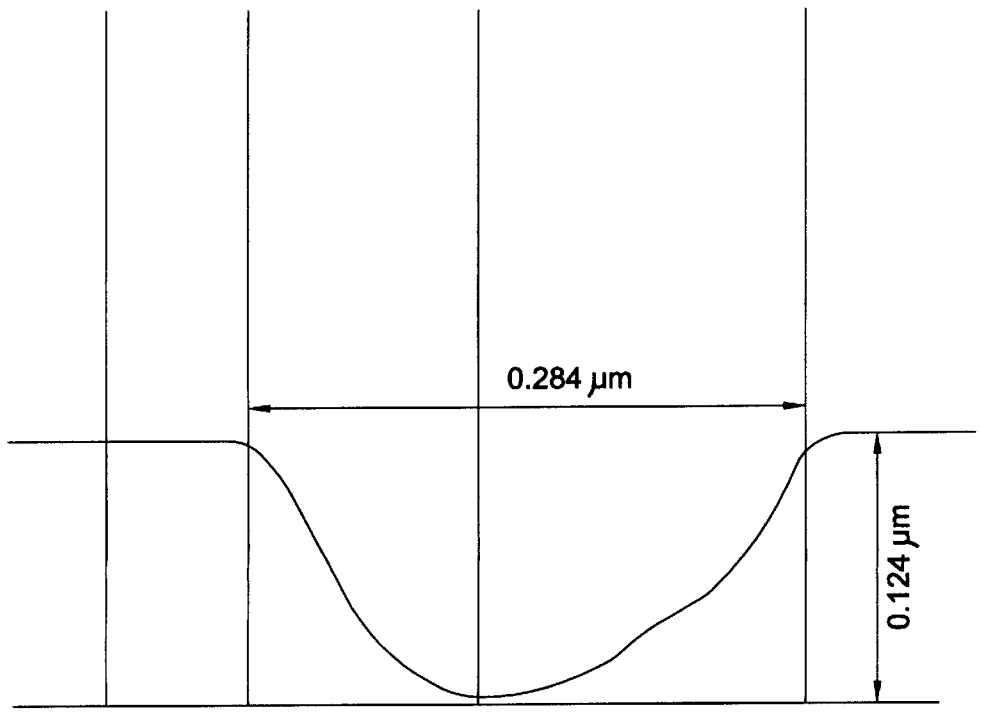
FIG. 9A illustrates COP morphology in a wafer using a conventional AFM technique.
Figure 9B:
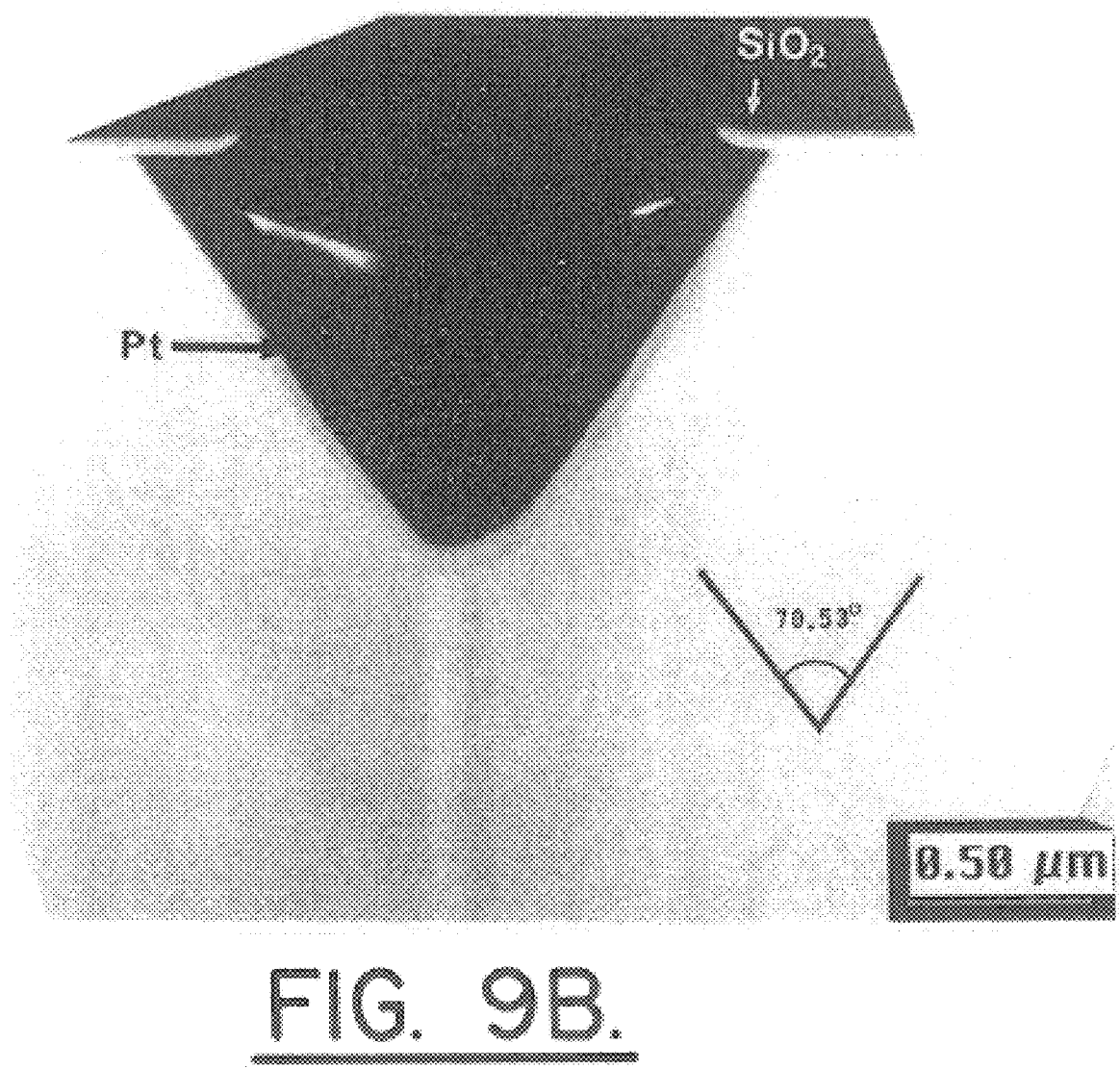
FIG. 9B illustrates a TEM-image of the morphology of a defect in a wafer after a Cu-decoration step according to the invention.

FIG. 9A illustrates COP morphology in a wafer using a conventional AFM technique, and FIG. 9B illustrates a TEM-image of the D-defect morphology in a wafer after a Cu-decoration according to the invention. It is believed that the COP map of the defect distribution by conventional LSPC may be able to accurately determine the diameter of the defect vacancy area on the wafer. Moreover, the positions of the defects may not be able to be accurately determined due to the presence of contaminants (e.g., particles) and due to the detection limit of the LSPC. Accordingly, there is a potentially poor correlation between the LSPC and the AFM. Thus, as illustrated in FIG. 9A, it may be difficult to accurately analyze the COP morphology in the wafer.

Referring to FIG. 9B, a TEM-image of defect morphology in a wafer after Cu-decoration is presented. As shown, the oxide film lifts along the defect edge. Defects depicted include: (1) D-defects having a capping layer and the direction of [111] in the silicon bulk, and (2) regular square pits which may be referred to as COPs. Copper may be deposited on sites containing the defects and thereafter the Cu diffuses in the silicon bulk in the wafer in the direction [111] by utilizing a locally-applied bias. A Cu-precipitate thus forms and Cu-decoration occurs. In addition, the platinum surface depicted in FIG. 9B becomes plated in order to minimize a charge phenomenon occurring in the wafer sample during TEM analysis.

The present invention presents a number of potential advantages. The distribution and density of defect-sites in an integrated circuit device may be analyzed without the aid of magnification. Moreover, since the real sizes and positions of the defects may be evaluated, the morphology and sizes of the defects can be analyzed more reliably relative to conventional methods by employing a transmission electron microscope or a scanning electron microscope. The detection limit of defects in the wafers may be increased, with defect sizes as low as 0.06 $\mu$m being potentially investigated. In addition, the generation of defect formation during wafer engineering may be suppressed by utilizing feedback information obtained with respect to the distribution, density, and morphology of wafer defects determined according to the methods of the invention.

In the drawings and specification, there have been disclosed typical preferred embodiments of the invention and, although specific terms are employed, they are used in a generic and descriptive sense only and not for the purposes of limitation, the scope of the invention being set forth in the following claims.

That which is claimed:

1. A method of treating a wafer for analyzing a defect present therein, said method comprising:

providing a wafer having a front side surface and a back side surface opposite thereto, the front side surface of the wafer comprising a defect-containing portion;

forming an insulation film on the front side surface of the wafer;

etching the back side surface of the wafer; and decorating the defect-containing portion of the front side surface of the wafer with copper.

2. A method according to claim 1, further comprising the step of cleaning the wafer prior to said step of forming the insulation film on the wafer.

3. A method according to claim 2, wherein said cleaning step is performed by contacting the wafer with an aqueous solution comprising ammonium hydroxide, hydrogen peroxide, and hydrogen fluoride.

4. A method according to claim 1, wherein the thickness of the insulation film ranges from about 250 Å to 1500 Å.

5. A method according to claim 1, wherein the thickness of the insulation film ranges from about 500 Å to about 1200 Å.

6. A method according to claim 1, wherein said etching step is performed on a portion of the back side surface of the wafer.

7. A method according to claim 1, wherein said etching step is performed using hydrogen fluoride.

8. A method according to claim 1, further comprising the step of cleaning the wafer with water subsequent to said etching step.

9. A method according to claim 1, wherein said wafer is a silicon crystal wafer.

10. A method according to claim 1, further comprising the step of analyzing the defect-containing portion present in the wafer subsequent to said decorating step.

11. A method according to claim 10, wherein the morphology of the defects present in the wafer are analyzed using an electron microscope.

12. A method according to claim 10, wherein the defects are selected from the group consisting of D-defects, crystal originated particle defects, and mixtures thereof.

13. A method according to claim 1, wherein said decorating step comprises:

loading a dummy wafer into a decoration device, the decoration device comprising an upper plate, a lower plate opposite thereto, and side walls which surround the upper and lower plates, the upper and lower plates comprising copper;

injecting an electrolyte into the decoration device;

applying a voltage to the upper and lower plates to ionize the copper contained on the upper and lower plates;

unloading the dummy wafer from the decoration device;

loading the wafer having the defective portion on the front side surface of the wafer into the decoration device; and applying a voltage to the upper and lower plates of the decoration device.

14. A method according to claim 13 wherein the electrolyte is methanol.

15. A method according to claim 13, wherein the said step of applying a voltage to the upper and lower plates of the decoration device comprises applying a voltage such that an electrical field results ranging from about 3 to MV/cm to about 10 MV/cm.

16. A method of treating a wafer for analyzing a defect present therein, said method comprising:

providing a wafer having a front side surface and a back side surface opposite thereto, the front side surface comprising a defect-containing portion;

forming an insulation film on the front side surface of the wafer;

etching the back side surface of the wafer; and removing the insulation film from the wafer to expose the defect-containing portion; and contacting the exposed defect-containing portion of the wafer with an electrolyte.

17. A method according to claim 16, wherein the insulation film is an oxide film.

18. A method according to claim 16, wherein said contacting step comprises forming an electric field on the front side surface and the lower side of the wafer.

19. A method according to claim 18, wherein the electric field ranges from about 3 to about 10 MV/cm.

20. A method according to claim 16, wherein the electrolyte is methanol.

21. A method according to claim 16, wherein the wafer is a silicon crystal wafer.

22. A method according to claim 16, further comprising the step of analyzing defects present in the defect-containing portion in the wafer subsequent to said contacting step.

23. A method according to claim 22, wherein the morphology of the defects present in the wafer are analyzed using an electron microscope.

24. A method according to claim 16, wherein the defect-containing portion comprises defects selected from the group consisting of D-defects, crystal originated particle defects, and mixtures thereof.

* * * * *